(12) United States Patent  
Maa et al.

(10) Patent No.: US 12,127,314 B2
(45) Date of Patent: Oct. 22, 2024

(54) COLOR TEMPERATURE FUSION LIGHTING APPARATUS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 147 days.

(21) Appl. No.: 18/101,569

(22) Filed: Jan. 25, 2023

(65) Prior Publication Data

US 2023/0164893 A1 May 25, 2023

Related U.S. Application Data

(63) Continuation-in-part of application No. 17/981,123, filed on Nov. 4, 2022, now Pat. No. 12,048,078, which is a continuation-in-part of application No. 17/509,877, filed on Oct. 25, 2021, now abandoned, which is a continuation-in-part of application No. 17/148,277, filed on Jan. 13, 2021, now Pat. No. 11,191,863, which is a continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(51) Int. Cl.
*H05B 45/20* (2020.01)
*A61N 5/06* (2006.01)
*G10K 15/04* (2006.01)
*H05B 47/155* (2020.01)

(52) U.S. Cl.
CPC .......... *H05B 45/20* (2020.01); *A61N 5/0618* (2013.01); *G10K 15/04* (2013.01); *H05B 47/155* (2020.01); *A61N 2005/0663* (2013.01)

(58) Field of Classification Search
CPC ...... H05B 45/10; H05B 45/20; H05B 45/325; H05B 45/3578; H05B 45/36; H05B 45/3725; H05B 45/375; H05B 45/38; H05B 45/385; H05B 45/60; H05B 47/175; H05B 45/24; H05B 45/395; H05B 47/105; H05B 47/11; H05B 47/16; H05B 47/19
See application file for complete search history.

(56) References Cited

U.S. PATENT DOCUMENTS

| | | | |
|---|---|---|---|
| 2010/0001648 A1* | 1/2010 | De Clercq | H05B 45/20 315/294 |
| 2017/0105265 A1* | 4/2017 | Sadwick | H05B 47/11 |

\* cited by examiner

*Primary Examiner* — Monica C King
(74) *Attorney, Agent, or Firm* — Andy M. Han; Han IP PLLC

(57) ABSTRACT

A color temperature fusion lighting apparatus includes a first light source with a first color temperature, a second light source with a second color temperature, and a driver circuit. The driver circuit operates the lighting apparatus in two modes. In the first mode, the driver circuit operates the lighting apparatus in a first linear combination of the first light source and the second light source, resulting in a first operating color temperature for the lighting apparatus. In the second mode, the driver circuit operates the lighting apparatus in a second linear combination of the first light source and the second light source, resulting in a second operating color temperature. Moreover, the driver circuit is configured to alternate the operation of the lighting apparatus between the first mode and the second mode at a frequency F between 35 to 45 Hz, resulting in a blended color temperature of the first operating color temperature and the second operating color temperature for the lighting apparatus.

16 Claims, 3 Drawing Sheets

Circadian Schedule

| Start Time | Stop Time | Target BCT | CTD |
|---|---|---|---|
| 00:00 | 07:00 | 3600K | 200K |
| 07:00 | 09:00 | 4000K | 200K |
| 09:00 | 17:00 | 4400K | 200K |
| 17:00 | 19:00 | 4000K | 300K |
| 19:00 | 00:00 | 3600K | 200K |

Circadian Schedule

| Start Time | Stop Time | Target BCT | CTD |
|---|---|---|---|
| 00:00 | 07:00 | 3600K | 200K |
| 07:00 | 09:00 | 4000K | 200K |
| 09:00 | 17:00 | 4400K | 200K |
| 17:00 | 19:00 | 4000K | 300K |
| 19:00 | 00:00 | 3600K | 200K |

FIG. 5

COLOR TEMPERATURE FUSION LIGHTING APPARATUS

CROSS REFERENCE TO RELATED PATENT APPLICATIONS

The present disclosure is a continuation-in-part (CIP) of U.S. patent application Ser. No. 17/981,123, filed 4 Nov. 2022. Content of aforementioned application is herein incorporated by reference in its entirety.

BACKGROUND

Technical Field

The present disclosure pertains to the field of lighting apparatuses and, more specifically, proposes a color temperature fusion lighting apparatus.

Description of Related Art

It has been discovered that by flickering a light at a frequency between 35 to 45 Hz or generating a sound at a similar frequency has the effect of stimulating the cells in certain region of the brain, resulting in using a flicking light or a sound at such a frequency for treating Alzheimer's disease. In U.S. patent application Ser. No. 17/981,123, a spectral power distribution (SPD) fusion lighting apparatus was introduced. It includes a first visible light source with a first SPD, a second visible light source with a second SPD, a driver circuit, and a controller. The first SPD is different than the second SPD markedly in a 50 nm wavelength range. The controller toggles the turning on of the first visible light and the second visible light at a frequency greater than 25 Hz. The first visible light source is turned on during one half of the duty cycle, whereas the second visible light source is turned on during the other half of the duty cycle. The first visible light source and the second visible light emit similar light outputs and have similar chromaticity coordinates on the CIE 1931 color space chromaticity diagram.

The SPD fusion lighting apparatus introduced in U.S. patent application Ser. No. 17/981,123 is very strict in that the first visible light source and the second visible light source must have similar chromaticity coordinates on the CIE 1931 color space chromaticity diagram and at the same time they must have markedly different SPDs in a 50 nm wavelength range. Only custom-made LED light sources could meet these conditions, thus resulting a higher production cost and subsequently a higher end user price.

It is known that when strobing two light sources each with a different color at a frequency greater than 25 Hz, human eyes cannot distinguish the individual colors. Human visual system would blend the two colors into a third color. It is thus conceivable of using the two light sources with similar yet sufficiently different color temperatures and strobing them at 35 to 45 Hz to create a color temperature fusion between the two color temperatures such that the human eyes can't pick out the individual color temperatures of the two light sources and yet their color temperature difference could still be picked up by the non-visual photoreceptor of the eyes, namely intrinsically photosensitive retinal ganglion cells (ipRGCs), resulting in a stimulation of the brain cells just like the turning on/off of a light source at 35 to 45 Hz, yet without the discomfort to the eyes.

The present disclosure proposes a lighting apparatus that strobes two light sources with similar yet sufficiently different color temperatures at a frequency between 35 to 45 Hz, such that human eyes could not pick up the visual difference of the two light sources, but the iRGCs still detect the difference between the two color temperatures, leading to a sufficient stimulation of certain brain cells. The present disclosure relaxes the restriction of using two light sources having similar chromaticity coordinates but markedly different SPDs as introduced in U.S. patent application Ser. No. 17/981,123. The present disclosure can thus be implemented using regular LED light sources with similar yet sufficiently different color temperatures, resulting in a lower production cost and a lower price point for the consumers.

SUMMARY

In one aspect, the color temperature fusion lighting apparatus comprises a first light source with a first color temperature CT1, a second light source with a second color temperature CT2, different from the first color temperature CT1, and a driver circuit. The driver circuit is configured to operate the lighting apparatus in two modes: the first mode and the second mode. In first mode, the driver is configured to operate the lighting apparatus in a first linear combination of the first light source and the second light source, resulting in a first operating color temperature OCT1 for the lighting apparatus (i.e., $OCT1 \approx X1*CT1+Y1*CT2$, where $X1+Y1=100\%$). Note that the color temperature scale is nonlinear, so the linear combination representation of two color temperatures is only an approximation. In the second mode, the driver is configured to operate the lighting apparatus in a second linear combination of the first light source and the second light source, different from the first linear combination, resulting in a second operating color temperature OCT2 for the lighting apparatus, different from the first operating color temperature OCT1 (i.e., $OCT2 \approx X2*CT1+Y2*CT2$, where $X2+Y2=100\%$, $X1 \neq X2$, and $Y1 \neq Y2$). The difference between the first operating color temperature OCT1 and the second operating color temperature OCT2 is greater than 100 Kelvin. This is so that there is sufficient color temperature difference to trigger the stimulation of the ipRGCs. Moreover, the driver circuit is configured to alternate the operation of the lighting apparatus between the first mode and the second mode at a frequency F between 35 to 45 Hz, resulting in a blended color temperature (or a color temperature fusion) for the light apparatus equal to $(OCT1+OCT2)/2$.

Here are four examples. For the first example, CT1=3900K and CT2=4100K. In the first mode, the driver circuit is configured to operate the lighting apparatus according to $OCT1 \approx 100\%*CT1+0\%*CT2=3900K$. In the second mode, the driver circuit is configured to operate the lighting apparatus according to $OCT2 \approx 0\%*CT1+100\%*CT2=4100K$. The driver circuit alternates the first mode and the second mode at 40 Hz frequency to produce a blended color temperature 4000K for the lighting apparatus.

For the second example, CT1=3500K and CT2=4500K. In the first mode, the driver circuit is configured to operate the lighting apparatus according to $OCT1 \approx 60\%*CT1+40\%*CT2=3900K$. In the second mode, the driver circuit is configured to operate the lighting apparatus according to $OCT2 \approx 40\%*CT1+60\%*CT2=4100K$. The driver circuit alternates the first mode and the second mode at 40 Hz frequency to produce a blended color temperature 4000K for the lighting apparatus.

For the third example, CT1=3900K and CT2=4300K. In the first mode, the driver circuit is configured to operate the lighting apparatus according to $OCT1 \approx 100\%*CT1+$ 0%*CT2=3900K. In the second mode, the driver circuit is configured to operate the lighting apparatus according to OCT2≈50%*CT1+50%*CT2=4100K. The driver circuit alternates the first mode and the second mode at 40 Hz frequency to produce a blended color temperature 4000K for the lighting apparatus.

For the fourth example, CT1=3800K and CT2=4200K. In the first mode, the driver circuit is configured to operate the lighting apparatus according to OCT1≈100%*CT1+0%*CT2=3800K. In the second mode, the driver circuit is configured to operate the lighting apparatus according to OCT2≈0%*CT1+100%*CT2=4200K. The driver circuit alternates the first mode and the second mode at 40 Hz frequency to produce a blended color temperature 4000K for the lighting apparatus.

It can be seen with the examples above that the present disclosure affords unlimited choices of the first color temperature and the second color temperature to produce the same first operating color temperature and the second operating color temperature and the same blended color temperature for the lighting apparatus. Even with different sets of the first operating color temperature and the second operating color temperature, it is still possible to produce the same blended color temperature for the lighting apparatus.

In some embodiments, the first operating color temperature OCT1 equals to the first color temperature CT1. In other words, OCT1≈X1*CT1+Y1*CT2, where X1=100% and Y1=0%. The first, the third, and the fourth examples above meet this condition.

In some embodiments, the second operating color temperature OCT2 equals to the second color temperature CT2. In other words, OCT2≈X2*CT1+Y2*CT2, where X2=0% and Y2=100%. The first and the fourth examples above meet this condition.

In some embodiments, the difference between the first operating color temperature and the second operating color temperature is less than 500 Kelvin. This condition is to make sure that the first operating color temperature and the second operating color temperature do not differ by too much. The first, the second, and the third examples stated above meet this condition.

In some embodiments, the difference between the first color temperature and the second color temperature is greater than 500 Kelvin. This condition makes sure the first color temperature and the second color temperature are sufficiently different, thus leading to the first operating color temperature and the second operating color temperature being sufficiently different. The second, the third, and the fourth examples mentioned above meet this condition.

Comparing the first example and the fourth example stated above, both produce the same blended color temperature 4000K. However, the fourth example has a wider difference between the first operating color temperature and the second operating color temperature (3800K vs. 4200K), as compared to the first example (3900K vs. 4100K). As a result, the fourth example may create a stronger stimulation to ipRGCs than that of the first example. While this may be desirable for most people, for some people with a higher visual sensitivity, the wider color temperature difference (3800K vs 4200K) may lead to visual discomfort and thus is less desirable. This suggests the need of supporting an adjustable color temperature difference between the first operating color temperature and the second operating color temperature, given a fixed blended color temperature for the lighting apparatus. This would afford each user to set his/her maximal tolerable color temperature difference between the first operating color temperature and the second operating color temperature, resulting the best personal Alzheimer treatment.

In some embodiments, the driver circuit is configured to support a target blended color temperature BCT and a color temperature difference CTD between the first operating color temperature and the second operating color temperature. The driver circuit automatically formulates the first linear combination of the first and the second light sources to produce the first operating color temperature OCT1 equal to BCT−(CTD/2). The driver circuit also automatically formulates the second linear combination of the first and the second light sources to produce the second operating temperature OCT2 equal to BCT+(CTD/2).

For example, CT1=3500K and CT2=4500K for an embodiment of the present disclosure. Moreover, a target BCT is set to 4000K and CTD to 200K. Then, OCT1=BCT−(CTD/2)=4000K−(200K/2)=3900K, and OCT2=BCT+(CTD/2)=4000K+(200K/2)=4100K. The driver circuit can automatically formulate the first linear combination of the first light source and the second light source as 60%*CT1+40%*CT2=3900K, equal to OCT1. Similarly, the driver circuit can automatically formulate the second linear combination of the first light source and the second light source as 40%*CT1+60%*CT2=4100K, equal to OCT2. When the driver circuit alternates the operation of the lighting apparatus between the first mode and the second mode at a frequency F between 35 to 45 Hz, the lighting apparatus produces a blended color temperature 4000K.

If for the same embodiment, BCT is set to 4000K and CTD to 400K, then, OCT1=BCT−(CTD/2)=4000K−(400K/2)=3800K, and OCT2=BCT+(CTD/2)=4000K+(400K/2)=4200K. The driver circuit can automatically formulate the first linear combination of the first light source and the second light source as 70%*CT1+30%*CT2=3800K, equal to OCT1. Similarly, the driver circuit can automatically formulate the second linear combination of the first light source and the second light source as 30%*CT1+70%*CT2=4200K, equal to OCT2. When the driver circuit alternates the operation of the lighting apparatus between the first mode and the second mode at a frequency F between 35 to 45 Hz, the lighting apparatus produces a blended color temperature 4000K.

The target blended color temperature BCT and the color temperature difference CTD may be embedded in the lighting apparatus. In order for them to be adjustable, it is necessary to have a user interface for configuring them. Therefore, in some embodiments, the lighting apparatus further comprises a user interface working in conjunction with the driver circuit for setting a target blended color temperature BCT and a color temperature difference CTD between the first operating color temperature and the second operating color temperature. BCT and CTD may be stored locally in a memory storage module in the lighting apparatus or remotely in a software application.

In some embodiments, the driver circuit is configured to support multiple target blended color temperatures BCTs. For example, CT1=3500K and CT2=4500K for an embodiment of the present disclosure, and CTD is set to 200K. It is demonstrated earlier that the driver circuit can support a BCT 4000K by formulating OCT1=60%*CT1+40%*CT2=3900K and OCT2=40%*CT1+60%*CT2=4100K. Similarly, the driver circuit can support a BCT at 3600K and a CTD at 200K by formulating OCT1=100%*CT1+0%*CT2=3500K and OCT2=80%*CT1+20%*CT2=3700K. When the driver circuit alternates the operation of the lighting apparatus between the first mode and the second mode at a frequency F between 35 to 45 Hz, the lighting apparatus produces a blended color temperature 3600K. Alternatively, the driver circuit can also support a BCT at 4400K and a CTD at 200K by formulating OCT1=20%*CT1+80%*CT2=4300K and OCT2=0%*CT1+100%*CT2=4500K. When the driver circuit alternates the operation of the lighting apparatus between the first mode and the second mode at a frequency F between 35 to 45 Hz, the lighting apparatus produces a blended color temperature 4400K.

Further in some embodiments, the driver circuit is configured to support multiple target blended color temperatures according to a circadian schedule. The circadian schedule may be stored locally in the lighting apparatus via a memory storage module, or remotely in a scheduling software app with a communication means (wired or wireless) to the lighting apparatus. With the example stated above, three BCTs (3600K, 4000K, and 4400K) can be supported by the lighting apparatus of the present disclosure. The driver circuit may support a circadian schedule as the following:

00:00-07:00: 3600K
07:00-09:00: 4000K
09.00-17:00: 4400K
17:00-19:00: 4000K
19:00-00:00: 3600K

In some embodiments, the light outputs (in lumens) of the lighting apparatus operating in the first mode and in the second mode are approximately the same (i.e., less than 10% difference). This would minimize the visual discomfort when the lighting apparatus is strobing between the first operating color temperature in the first mode and the second operating color temperature in the second mode.

In some embodiments, the driver circuit converts an AC mains power to a first internal DC power with the operating frequency F for driving the first light source and to a second internal DC power with the operating frequency F for driving the second light source.

In some embodiments, the second internal DC power has a 180-degree phase shift from the first internal DC power. Further in some embodiments, the driver circuit comprises an inverter for converting the first internal DC power to the second internal DC power, thus guaranteeing the second internal DC power having a 180-degree phase shift from the first internal DC power.

In some embodiments, the first light source comprises light emitting diode (LED) and the second light source comprises LED. LED is a preferred light source medium because it can be turned on/off instantaneously and thus suitable for operating at an on/off frequency between 35 to 45 Hz.

In some embodiments, the apparatus further comprises a sound wave generator for generating a sound wave at the same frequency F that the driver circuit alternates the lighting apparatus between the first mode and the second mode. Having both visual and audible stimulations could potentially double the effect of stimulating certain brain cells, resulting a more effective treatment to Alzheimer's disease.

Further in some embodiments, the sound wave generator generates a sinusoidal sound wave, as opposed to a square sound wave. A square sound wave is harsher and less comfortable to ears as compared to a sinusoidal sound wave. Thus, using a sinusoidal sound wave may lead to a better user adoption or a longer treatment time, resulting a more effective treatment of Alzheimer's disease.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

FIG. 5 is an example of the circadian schedule.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses a color temperature fusion lighting apparatus that includes a first light source with a first color temperature, a second light source with a second color temperature, and a driver circuit. The driver circuit operates the lighting apparatus in two modes. In the first mode, the driver circuit operates the lighting apparatus in a first linear combination of the first light source and the second light source, resulting in a first operating color temperature for the lighting apparatus. In the second mode, the driver circuit operates the lighting apparatus in a second linear combination of the first light source and the second light source, resulting in a second operating color temperature. Moreover, the driver circuit is configured to alternate the operation of the lighting apparatus between the first mode and the second mode at a frequency F between 35 to 45 Hz, resulting in a blended color temperature (i.e., a color temperature fusion) of the first operating color temperature and the second operating color temperature for the lighting apparatus.

Example Implementations

Figure 1:
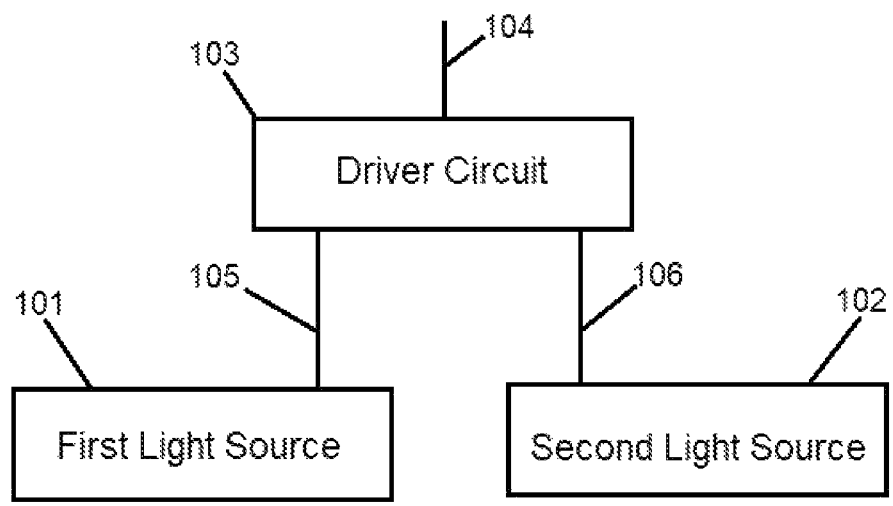
FIG. 1 schematically depicts a first embodiment of the present disclosure.

FIG. 1 is an embodiment of the color temperature fusion lighting apparatus of the present disclosure. The embodiment 100 has a first light source 101, a second light source 102, and a driver circuit 103. The first light source 101 comprises 3900K LEDs (i.e., CT1=3900K) and the second light source 102 comprises 4100K LEDs (i.e., CT2=4100K). The driver circuit 103 converts the AC mains 104 into two internal DC powers 105 and 106. The first internal DC power 105 supplies power to drive the first light source 101 and the second internal DC power 106 supplies power to drive the second light source 102. The second internal DC power 106 has a 180-degree phase shift from the first internal DC power 105. The driver circuit 103 operates the lighting apparatus in two modes. In the first mode, only the first light source 101 is turned on (i.e., OCT1=3900K), whereas in the second mode, only the second light source 102 is turned on (i.e., OCT2=4100K). Moreover, the driver circuit 103 alternates the operation of the lighting apparatus between the first mode and the second mode at a frequency 40 Hz to produce a blended color temperature at 4000K for the light apparatus.

In a second embodiment, the lighting apparatus 100 uses 3800K LEDs as its first light source 101 and 4200K LEDs as its second light source 102. For this second embodiment, OCT1=3800K and OCT2=4200K. The driver circuit 103 alternates the operation of the lighting apparatus between the first mode and the second mode at a frequency 40 Hz, resulting in a blended color temperature at 4000K for the light apparatus.

Figure 2:
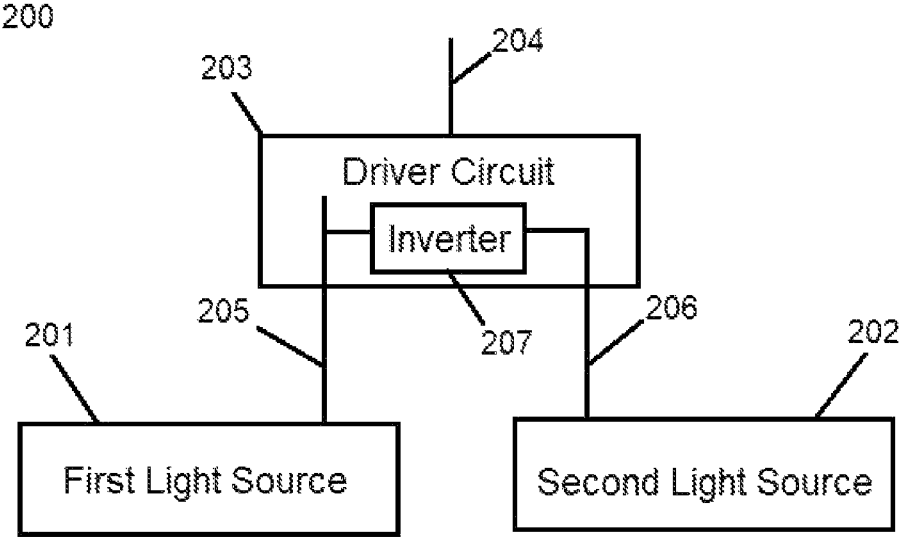
FIG. 2 schematically depicts a second embodiment of the present disclosure.

FIG. 2 is another embodiment of the color temperature fusion lighting apparatus of the present disclosure. The embodiment 200 is exactly the same as the embodiment 100 with the only exception that the driver circuit 203 also includes an inverter 207 for phase-shifting the first internal DC power 205 by 180-degree to create the second internal DC power 206.

Figure 3:
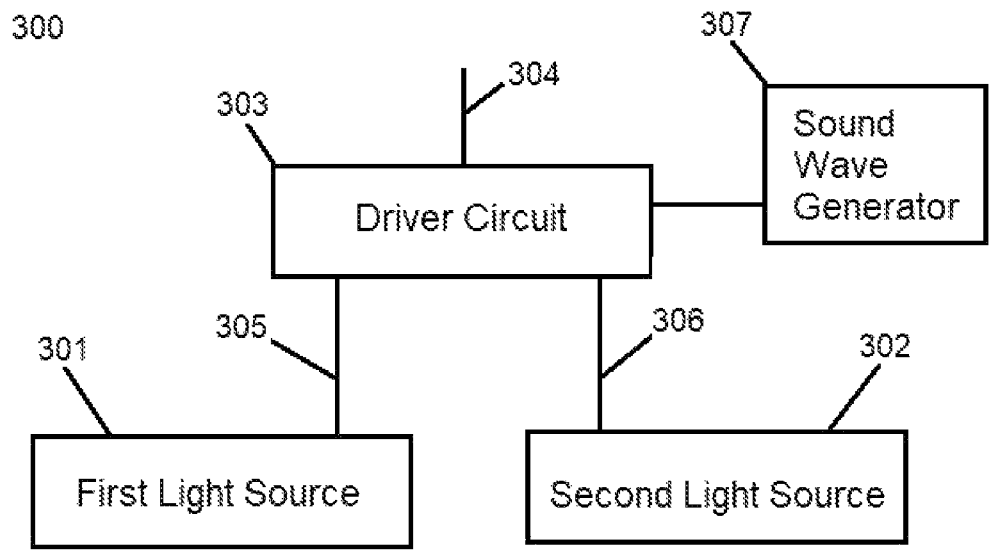
FIG. 3 schematically depicts a third embodiment of the present disclosure.

FIG. 3 is another is another embodiment of the color temperature fusion lighting apparatus of the present disclosure. This embodiment 300 has a first light source 301, a second light source 302, a driver circuit 303, and a sound wave generator 307. The first light source 301 comprises 3500K LEDs (i.e., CT1=3500K) and the second light source 302 comprises 4500K LEDs (i.e., CT2=4500K). The driver circuit 303 converts the AC mains 304 into two internal DC powers 305 and 306. The first internal DC power 305 supplies power to drive the first light source 301 and the second internal DC power 306 supplies power to drive the second light source 302. The second internal DC power 306 has a 180-degree phase shift from the first internal DC power 305. The driver circuit 303 operates the lighting apparatus in two modes. In the first mode, the driver circuit 303 is operates the lighting apparatus according to OCT1≈60%*CT1+40%*CT2=3900K. In the second mode, the driver circuit 303 operates the lighting apparatus according to OCT2≈40%*CT1+60%*CT2=4100K. Moreover, the driver circuit 303 alternates the first mode and the second mode at 40 Hz frequency to produce a blended color temperature 4000K for the lighting apparatus. The driver circuit 303 also triggers the sound wave generator 307 to generate a sinusoidal sound wave at 40 Hz.

For the embodiment 300, it is conceivable to change the first light source 301 to 3900K LEDs (i.e., CT1=3900K) and the second light source 302 to 4300K (i.e., CT2=4300K), and modify the driver circuit 303 such that In the first mode the driver circuit operates the lighting apparatus 300 according to OCT1≈100%*CT1+0%*CT2=3900K, and in the second mode the driver circuit operates the lighting apparatus according to OCT2≈50%*CT1+50%*CT2=4100K. The driver circuit 303 alternates the first mode and the second mode at 40 Hz frequency to produce a blended color temperature 4000K for the lighting apparatus 300.

Figure 4:
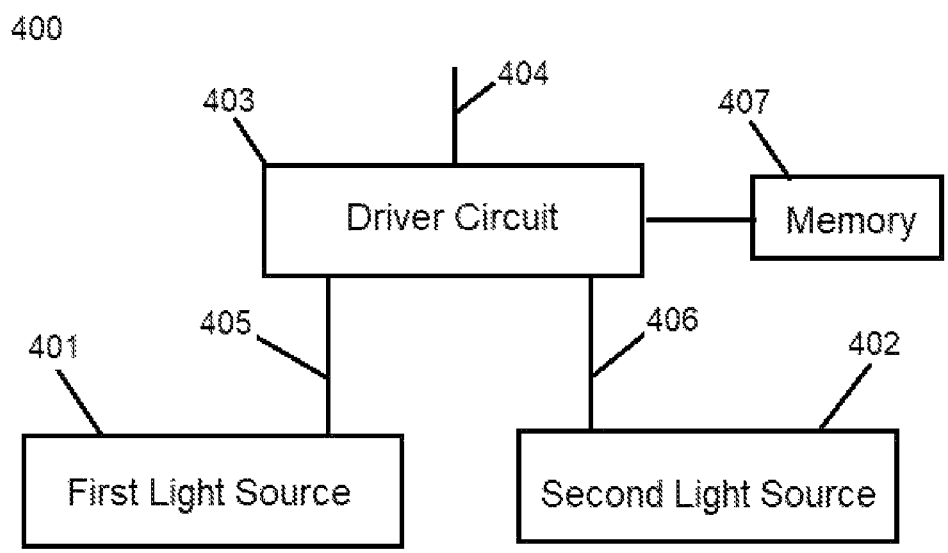
FIG. 4 schematically depicts a fourth embodiment of the present disclosure.

FIG. 4 is another embodiment of the color temperature fusion lighting apparatus of the present disclosure. The embodiment 400 has a first light source 401, a second light source 402, and a driver circuit 403. The first light source 401 comprises 3500K LEDs (i.e., CT1=3500K) and the second light source 402 comprises 4500K LEDs (i.e., CT2=4500K). The driver circuit 403 converts the AC mains 404 into two internal DC powers 405 and 406. The first internal DC power 405 supplies power to drive the first light source 401 and the second internal DC power 406 supplies power to drive the second light source 402. The second internal DC power 406 has a 180-degree phase shift from the first internal DC power 405. Additionally, a user can use an app on a mobile device to set a circadian schedule for the embodiment 400. FIG. 5 is an example of the circadian schedule. The circadian schedule is transmitted to the embodiment 400 via Wi-Fi communications (though not shown), and the circadian schedule is stored in the memory module 407. The driver circuit 403 will operate according to the circadian schedule shown in FIG. 5. For each pair of a target BCT and a CTD, the driver circuit 403 calculates OCT1=BCT−(CTD/2) and formulate automatically the first linear combination of the first light source and the second light source to produce the first operating color temperature OCT1. Similarly, the driver circuit 403 calculates OCT2=BCT+(CTD/2) and formulate automatically the second linear combination of the first light source and the second light source to produce the second operating color temperature OCT2. For example, for the period between 00:00 to 07:00, BCT is 3600K and CTD is 200K. The driver circuit 403 can formulate OCT1=100%*CT1+0%*CT2=3500K and OCT2=80%*CT1+20%*CT2=3700K. As the driver circuit 403 alternates the operation of the embodiment 400 between the first mode and the second mode at a frequency 40 Hz, the embodiment 400 produces a blended color temperature 3600K.

Note that the CTD may be different for each period of the circadian schedule. This allows a user to schedule a period for a larger CTD to produce a stronger stimulation of ipRGCs during this period. For example, for the period 17:00 to 19:00, the target BCT is 4000K and CTD is 300K. In this case, the first linear combination is OCT1=65%*CT1+35%*CT2=3850K and the second linear combination is OCT2=35%*CT1+65%*CT2=4150K.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A color temperature fusion lighting apparatus, comprising
 a first light source with a first color temperature (CT1);
 a second light source with a second color temperature (CT2) different from the CT1; and
 a driver circuit, configured to operate the lighting apparatus in two modes:
  in a first mode, the driver circuit is configured to operate the lighting apparatus in a first linear combination of the first light source and the second light source, resulting in a first operating color temperature (OCT1) of the lighting apparatus, such that $OCT1 \approx X1*CT1+Y1*CT2$, wherein $X1+Y1=100\%$;

in a second mode, the driver circuit is configured to operate the lighting apparatus in a second linear combination of the first light source and the second light source, different from the first linear combination, resulting in a second operating color temperature (OCT2) of the lighting apparatus, different from the first operating color temperature OCT1, such that $OCT2 \approx X2*CT1+Y2*CT2$, wherein $X2+Y2=100\%$, X1 #X2, and Y1 #Y2;

wherein:

a difference between the OCT1 and the OCT2 is greater than 100 Kelvin, and the driver circuit is configured to alternate an operation of the lighting apparatus between the first mode and the second mode at a frequency F between 35 Hz and 45 Hz, resulting in a blended color temperature of the light apparatus equal to (OCT1+OCT2)/2.

2. The lighting apparatus of claim 1, wherein the OCT1 equals to the CT1 such that $OCT1 \approx X1*CT1+Y1*CT2$, and wherein $X1=100\%$ and $Y1=0\%$.

3. The lighting apparatus of claim 1, wherein the OCT2 equals to the CT2 such that $OCT2 \approx X2*CT1+Y2*CT2$, and wherein $X2=0\%$ and $Y2=100\%$.

4. The lighting apparatus of claim 1, wherein the difference between the first operating color temperature and the second operating color temperature is less than 500 Kelvin.

5. The lighting apparatus of claim 1, wherein the difference between the first color temperature and the second color temperature is greater than 500 Kelvin.

6. The lighting apparatus of claim 1, wherein the driver circuit is configured to support a target blended color temperature (BCT) and a color temperature difference (CTD) between the first operating color temperature and the second operating color temperature by automatically formulating the first linear combination of the first light source and the second light source to produce the first operating color temperature OCT1 equal to BCT−(CTD/2) and formulating the second linear combination of the first light source and the second light source to produce the second operating temperature OCT2 equal to BCT+(CTD/2).

7. The lighting apparatus of claim 6, further comprising:

a user interface operating in conjunction with the driver circuit to set the BCT and the CTD between the first operating color temperature and the second operating color temperature.

8. The lighting apparatus of claim 6, wherein the driver circuit is configured to support multiple target blended color temperatures.

9. The lighting apparatus of claim 7, wherein the driver circuit is configured to support multiple target blended color temperatures according to a circadian schedule.

10. The lighting apparatus of claim 1, wherein light outputs of the lighting apparatus operating in the first mode and in the second mode are approximately the same with less than 10% difference.

11. The lighting apparatus of claim 1, wherein the driver circuit is further configured to convert an alternating-current (AC) mains power to a first internal direct-current (DC) power with the operating frequency (F) to drive the first light source and to a second internal DC power with the operating frequency to drive the second light source.

12. The lighting apparatus of claim 11, wherein the second internal DC power has a 180-degree phase shift from the first internal DC power.

13. The lighting apparatus of claim 12, wherein the driver circuit comprises an inverter configured to convert the first internal DC power to the second internal DC power.

14. The lighting apparatus of claim 1, wherein the first light source comprises a first light emitting diode (LED) and the second light source comprises a second LED.

15. The lighting apparatus of claim 1, further comprising:

a sound wave generator configured to generate a sound wave at a frequency F.

16. The lighting apparatus of claim 15, wherein the sound wave generator is configured to generate a sinusoidal sound wave.

* * * * *